United States Patent
Vogt et al.

(10) Patent No.: US 6,929,690 B2
(45) Date of Patent: Aug. 16, 2005

(54) PIGMENT WITH A METALLIC LUSTER

(75) Inventors: Reiner Vogt, Darmstadt (DE); Gerhard Pfaff, Münster (DE); Stephanie Andes, Hanau (DE); Michael Uhlig, Darmstadt (DE); Martin Friz, Darmstadt (DE); Katsuhisa Nitta, Iwaki (JP)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/493,409
(22) PCT Filed: Sep. 27, 2002
(86) PCT No.: PCT/EP02/10864
§ 371 (c)(1), (2), (4) Date: Apr. 22, 2004
(87) PCT Pub. No.: WO03/037993
PCT Pub. Date: May 8, 2003

(65) Prior Publication Data
US 2004/0244640 A1 Dec. 9, 2004

(30) Foreign Application Priority Data
Oct. 27, 2001 (DE) .......................... 101 53 196

(51) Int. Cl.$^7$ ................................ C09C 1/62
(52) U.S. Cl. ................ 106/403; 106/417; 106/431; 106/436; 106/439; 106/453; 106/454; 106/456; 106/415; 106/442; 106/446; 106/404

(58) Field of Search ................ 106/415, 417, 106/431, 436, 439, 453, 454, 456, 403, 404, 446, 442

(56) References Cited

U.S. PATENT DOCUMENTS

| | | |
|---|---|---|
| 6,267,810 B1 | 7/2001 | Pfaff et al. |
| 6,325,847 B1 * | 12/2001 | Christie et al. ............ 106/417 |
| 6,440,208 B1 * | 8/2002 | Christie et al. ............ 106/415 |
| 2004/0237844 A1 * | 12/2004 | Pfaff et al. ................. 106/415 |

FOREIGN PATENT DOCUMENTS

| | | | |
|---|---|---|---|
| EP | 1045014 A2 | 10/2000 | |
| WO | WO 9308237 | 4/1993 | |
| WO | WO 93/08237 * | 4/1993 | ............ C09C/1/00 |
| WO | WO 0140383 | 6/2001 | |

* cited by examiner

Primary Examiner—J. A. Lorengo
Assistant Examiner—S. S. Manlove
(74) Attorney, Agent, or Firm—Millen White Zelano & Branigan, P.C.

(57) ABSTRACT

A pigment with a metallic luster, comprising a wafer-like substrate made of aluminium dioxide having a thickness of more than 250 nm and less than 1 μm, which is fully enveloped by a metal layer.

20 Claims, No Drawings

PIGMENT WITH A METALLIC LUSTER

The invention relates to an effect pigment consisting of a platelet-shaped aluminium oxide substrate and a metal layer which completely surrounds the substrate. The invention furthermore relates to a process for the preparation of the pigment and to the use thereof.

Metal-effect pigments have been employed for many years in coatings for producing a metal effect. Classical metal-effect pigments consist of plate-let-shaped metal particles whose optical effect is based on directed reflection of incident light at metal particles which ideally have a flat shape and are aligned parallel in the respective application medium.

The main areas of application of metal-effect pigments are the automobile and printing industries. In addition, they are also employed for colouring plastics and paints, for leather coatings, in cosmetics and in the ceramics industry. In the car paints area, they are used mainly for producing the metallic effect, where they are usually applied together with other pigments, such as pearlescent pigments, titanium dioxide, carbon black or organic pigments, in the paint.

In order to be able to compare the quality of metallic or metal effects, for example in paints, printing inks and plastics, with one another, certain quality features have been defined. These are, inter alia, the brilliance (sparkle effect and metallic lustre), the brightness and the flop (change in brightness as a function of viewing angle), the distinctness of image, the colour saturation in coloured metallic coatings and the hiding power. The metal effect is influenced essentially by the particle shape and the form factor (ratio of mean particle diameter to mean particle thickness) of the pigments and their surface smoothness, the particle size, the particle size distribution and by the pigment orientation parallel to the surface of the paint or plastic and the like.

The optical impression is determined by the ratio of reflected light to scattered light. While relatively strong reflection, evident from the high metallic brilliance, improved brightness and strong flop, occurs in the case of relatively large pigment particles having a uniform shape, the scattered component is very high in fine pigments having an irregular particle structure, which results in improved distinctness of image and good hiding power.

However, there is now a demand for metal pigments which simultaneously have high brilliance and good hiding power and distinctness of image. This cannot be achieved by the metal pigments currently available, since in each case contradictory effects are observed depending on the particle size distribution.

Thus, the aluminium pigments traditionally employed, which are prepared by mechanical processes starting from aluminium powder, do not meet these requirements. Depending on the starting material and grinding method, non-uniform aluminium platelets having a large scattered component or rather round aluminium platelets are obtained. The round platelets (so-called silver dollars) have a relatively smooth surface and, owing to their small scattered component, can be employed for achieving improved metallic lustre and glitter effects. However, given the comparatively large particle diameters, good hiding power cannot be achieved. Silver dollars are available, for example, under the name Stapa® Metallux 2000 from Eckart.

However, particularly thin aluminium platelets produced by a PVD (physical vapour deposition) process have also been developed. These are described in greater detail in U.S. Pat. No. 3,949,139 and U.S. Pat. No. 4,321,087. Whereas conventional aluminium pigments have platelet thicknesses of greater than 100 nm, PVD pigments, for example the Metallure® grade from Eckart, have thicknesses of significantly less than 100 nm. The PVD aluminium pigments enable improved hiding power and a metal foil-like effect to be achieved compared with the conventional aluminium pigments.

However, their use requires very specific applicational know-how in order to achieve reproducible effects. Otherwise, problems occur during application of the pigments. Thus, as a consequence of their low mechanical stability, they can only be subjected to low shear forces during incorporation into application systems, for example paints or plastics. In addition, their use in water-based application systems is problematic owing to the large reactive surface as a consequence of production. For certain applications, they are moreover not suitable at all, for example for powder coating.

There has also been no lack of attempts to achieve metal effects by means of pigments which are not metal pigments in the conventional sense, for example with the classical interference pigments, which consist of transparent substrates and metal-oxide layers deposited thereon, or with interference pigments, which have one or more metal and/or metal-oxide layers on a metal core. A good, metal-like lustre can usually be produced with the former. However, since the substrates and all layers located thereon are transparent to a high degree, they have only low hiding power. The pigments consisting of a metal core with one or more metal and/or metal-oxide layers generally have good hiding power and a vivid colour flop. However, the processes for the preparation of such pigments are extremely complex and expensive.

EP 0 763 573 discloses a pearlescent pigment which consists of an aluminium oxide substrate with a titanium oxide component and a metal-oxide layer located thereon. This pigment is transparent and has high pearlescence. It is marketed under the name Xirallic® by Merck KGaA.

EP 1 013 724 discloses that pigments of the Xirallic® type, which may optionally also be coated with metals instead of metal oxides, can in certain areas of application advantageously be employed in combination with specific effect pigments, including metal pigments. This pigment combination is said to result in notable deep lustre, glitter effects and a strong colour flop, but it is dependent on the composition of the mixture. Good hiding power can only be achieved in this mixture if opaque pigments are added.

No pigments have been disclosed hitherto with which both a metallic optical impression with strong lustre which includes glitter effects, and good hiding power can be achieved simultaneously.

The object of the invention is therefore to provide a pigment having metallic lustre which can be employed without problems in all application systems, such as paints, plastics and print products, and provides the latter with an opaque, sparkling metallic appearance without the addition of further pigments.

This object is achieved in accordance with the invention by a pigment having metallic lustre which comprises a platelet-shaped aluminium oxide substrate having a thickness of greater than 250 nm and less than 1 µm which is completely surrounded by a metal layer.

This object is furthermore achieved by a process for the preparation of this pigment by suspending the substrate in an aqueous and/or solvent-containing medium in the presence of a metal compound and, after addition of a reducing agent, depositing the metal layer on the substrate.

This object is likewise achieved by a process for the preparation of this pigment by coating the substrate fluidised in a fluidised bed with metals obtained by gas-phase decomposition of the corresponding volatile metal compounds.

Finally, this object is achieved by a process for the preparation of this pigment by depositing the corresponding metals on the substrate in a high vacuum by sputtering or thermal vapour deposition, with the substrate being kept in uniform motion during the coating operation.

The invention furthermore relates to the use of the pigments according to the invention in paints, surface coatings, printing inks, plastics, cosmetic formulations, ceramic materials, glasses, paper, for laser marking of plastics, in security applications and in dry preparations and pigment preparations.

The substrates employed for the pigments according to the invention are aluminium oxide platelets which either consist entirely of aluminium oxide or alternatively may additionally comprise small proportions of other materials, such as, for example, titanium oxide.

These aluminium oxide platelets are produced by particular processes and therefore have a particularly smooth surface.

They have a thickness of greater than 250 nm and less than 1 $\mu$m, but preferably between 300 nm and 500 nm. This particle thickness can be adjusted via the reaction conditions in the production processes. If the particle thickness is less than 250 nm, the desired glitter effect of the pigments can no longer be achieved, since the particles are no longer perceptible as individual particles in the application medium.

However, if the particle thickness exceeds 1 $\mu$m, a smooth, highly reflective surface can no longer be ensured in the application medium since there is a risk of the pigments adopting an unfavourable alignment and thus of surface roughness occurring.

It is possible, for example, to use the $\alpha$-$Al_2O_3$ aluminium oxide platelets described in JP-B-03-72527, which have a mean particle diameter of from 500 nm to 3 $\mu$m.

It is likewise possible to employ the fine $Al_2O_3$ particles disclosed in JP-A-04-39362, in which the face in the hexagonal corundum lattice preferably grows perpendicular to the c axis, resulting in the formation of a platelet structure.

Preference is given to the $Al_2O_3$ substrates whose structure and production are described in EP 0 763 573. These comprise between 0.1 and 4% by weight of titanium oxide and preferably have a mean particle diameter of 5–60 $\mu$m, a thickness of less than 1 $\mu$m and a form factor of greater than 20. They are produced by a process in which the corresponding monocrystals are deposited by vapour deposition from an aqueous solution of a water-soluble aluminium salt in the presence of a water-soluble titanium salt and in the presence of an aqueous solution comprising an alkali-metal sulfonate and phosphoric acid or a phosphate, and are subsequently dried at high temperatures.

However, particular preference is given to the substrates described in Eur. Coat. J., April, 1999, pp. 90–96. $Al_2O_3$ substrate particles of this type, which are also known as alumina flakes, are synthesised from the salt melt by a crystal-growth process. To this end, hydrated aluminium oxide which has been doped with titanium oxide and phosphate is mixed with sodium sulfate in aqueous suspension and subsequently dried, giving a homogeneous powder. This powder is heated to up to 1200° C. in crucibles. A crystal-growth mechanism results in the formation of the alumina flakes in the form of monocrystals. After cooling, the soluble constituents are removed, and the $Al_2O_3$ platelets are isolated by filtration. The platelet-shaped particles formed in this way have an extraordinarily smooth surface and have very regular crystal shapes. They have no tendency towards twin-crystal formation or agglomeration and can be dispersed very well.

The mean diameter of the substrate particles is not crucial per se. It is usually in the range from 1 to 250 $\mu$m, preferably from 2 to 200 $\mu$m and in particular from 5 to 60 $\mu$m.

The form factor of the substrate particles is greater than 20, but preferably between 50 and 200.

For the metal layer surrounding the substrate, suitable metals are those which have a particularly strong reflection capacity. Preference is given to aluminium, titanium, chromium, nickel, silver, zinc, molybdenum, tantalum, tungsten, palladium, copper, gold, platinum and alloys thereof, for example Hastelloy. Particular preference is given to aluminium and silver.

The thickness of the metal layer is between 15 and 100 nm. It is preferably set to from 20 to 50 nm.

The metal layer can be applied by known wet-chemical methods by reduction of inorganic or organic metal compounds in a suspension of the substrate particles. However, it can also be deposited by a CVD (chemical vapour deposition) method, for example gas-phase decomposition of metal carbonyls, or by a PVD method, for example by sputtering or vapour deposition of metals.

In the case of wet-chemical deposition of the metal layer, the substrate is suspended in an aqueous and/or solvent-containing medium in the presence of a metal compound, and, after addition of a reducing agent, the metal is deposited on the substrate. The metal compound can be an inorganic compound, for example silver nitrate, or an organometallic compound, for example nickel acetylacetonate. The solvent to be used is determined by the solubility of the organometallic compound.

The process described in U.S. Pat. No. 3,536,520 uses nickel chloride in the aqueous phase, with the substrate (mica) being subjected to pre-treatment with tin chloride and palladium chloride. The reducing agent used is hypophosphite.

In EP 0 353 544, the reducing agents for the wet-chemical metal deposition are reducing compounds, such as aldehydes (formaldehyde, acetaldehyde or benzaldehyde), ketones (acetone), carboxylic acids and salts thereof (tartaric acid or ascorbic acid), reductones (isoascorbic acid, triose reductone or reductic acid) and reducing sugars (glucose). However, it is also possible to use reducing alcohols (allyl alcohol), polyols and polyphenols, sulfites, hydrogensulfites, dithionites, hypophosphites, hydrazine, boron nitrogen compounds, metal hydrides and complex hydrides of aluminium and boron.

The deposition of the metal layer can furthermore be carried out with the aid of a CVD method. Methods of this type are known. Fluidised-bed reactors are preferably employed for this purpose. EP 0 741 170 describes the deposition of aluminium layers by reduction of alkylaluminium compounds using hydrocarbons in a stream of inert gas. The metal layers can further-more be deposited by gas-phase decomposition of the corresponding metal carbonyls in a heatable fluidised-bed reactor, as described in EP 045 851. Further details on this method are given in WO 93/12182.

A further process for the deposition of thin metal layers which can be used in the present case for the application of the metal layer to the substrate is the known method for vapour deposition of metals in a high vacuum. It is described in detail in Vakuum-Beschichtung [Vacuum Coating], Volumes 1–5; Editors Frey, Kienel and Löbl, VDI-Verlag, 1995.

For the preparation of the lustre pigments according to the invention, it is absolutely necessary to match the high-vacuum vapour-deposition process to the substrate in powder form. To this end, it is necessary for the substrate to be kept uniformly in motion in the vacuum reactor during the vapour-deposition process in order to ensure homogeneous coating of all particle surfaces.

This is achieved, for example, through the use of rotating containers or the use of vibration devices.

In the sputtering process, a gas discharge (plasma) is ignited between the support and the coating material, which is in the form of plates (target). The coating material is bombarded with high-energy ions from the plasma, for example argon ions, and thus removed or atomised. The atoms or molecules of the atomised coating material are precipitated on the support and form the desired thin layer.

For sputtering processes, metals or alloys are particularly suitable. These can be atomised at comparatively high rates, in particular in the so-called DC magnetron process.

The latter is particularly preferred in the present invention for application of the metal layer to the substrate particles.

The sputtering process is described in Vakuum-Beschichtung [Vacuum Coating], Volumes 1–5; Editors Frey, Kienel and Löbl, VDI-Verlag, 1995.

If pigments having coloured metal effects are desired, it is possible to apply further layers of coloured or colourless metal oxides, metal nitrides, metal sulfides and/or metals to the metal layer. These layers are transparent or semitransparent and allow at least 10% of the incident light to pass through.

It is preferred in this case for layers of high refractive index and layers of low refractive index to be applied alternately or for a layer which has a refractive-index gradient within the layer thickness to be applied. The interference phenomena which occur in this case additionally cause an intense colour play and/or a strong colour flop, enabling the pigments to be employed advantageously in many areas of application.

For use in outdoor applications, in particular on use in vehicle paints, the pigments according to the invention can be provided with an additional weather-stabilising protective layer, the so-called post-coating, which simultaneously effects optimum adaptation to the binder system. Post-coatings of this type have been described, for example, in EP 0 268 918 and EP 0 632 109.

The pigments according to the invention enable, for the first time, both strong metallic lustre and good hiding power to be achieved simultaneously only with a single pigment, with the products coated, printed or coloured therewith also exhibiting strong sparkling, which is very desired, in particular, for automobile paints. It is not known precisely what this effect, which can also be referred to as "metallic crystal effect", is based on. However, it is assumed that the particularly smooth surface and the regular crystal shape of the substrates employed, which is also retained in the subsequent metallic coating, result in increased reflection of the incident light, which is why relatively small pigment areas compared with the known prior art are sufficient to achieve high metallic lustre and high brightness values as well as good brightness flop. However, the pigments are sufficiently large to be visually perceptible, at least in some cases, as individual particles, which results in a brightly sparkling optical impression.

However, the comparatively small diameter of the pigments overall and the set thickness of the particles result in sufficiently diffuse-scattering edges being present, which result in a high scattered-light content and thus in an opaque coating.

Besides the optical effects described, the pigments according to the invention also exhibit a number of other advantages. Thus, for example, their mechanical stability is greatly improved, in particular compared with the prior-art pigments prepared by PVD processes, through the stabilising non-metallic substrate. This is evident, for example, from low flexibility, which guarantees stably smooth surfaces without the latter becoming brittle. The mechanical stability ensures that no destruction of the pigments takes place in the various application systems, even on the mechanical loading of the particles through stirring, grinding or the like. They can also be employed without problems in the known pump line systems since they have only a low tendency to settle. Surprisingly, the pigments according to the invention can also be readily oriented in the application system although they have rather moderate layer thicknesses.

In addition, the processes described for the preparation of the pigments according to the invention are simple and comparatively inexpensive to carry out.

The pigments according to the invention are compatible with a multiplicity of colour systems, preferably in the area of surface coatings, paints and printing inks. They can likewise be employed for the laser marking of paper and plastics and in ceramic materials and for applications in the agricultural sector. Owing to their particular effects, however, they are particularly suitable for the automobile sector, the printing industry and decorative cosmetics. They can likewise be employed in the preparation of pigment preparations and dry preparations which are used, in particular, in printing inks and surface coatings. A further preferred area of application is the security sector with various applications, for example in bank notes, credit cards, visas, for tax seals or the like.

Although the pigments according to the invention themselves have excellent properties, they can of course also be used in the form of a blend with a very wide variety of commercially available pigments, for example organic or inorganic dyes, conventional transparent, coloured, black or white pigments, such as, for example, metal oxide-coated mica pigments, with holographic pigments, LCPs (liquid crystal polymers) or conventional metal pigments. In addition, they can be mixed in any ratio with commercially available pigments and fillers and/or binders.

The complete disclosure content of all patent applications, patents and publications mentioned above is incorporated into this application by way of reference.

The following examples are intended to explain the invention, but without restricting it.

EXAMPLES

Example 1

For a coating of aluminium oxide platelets with silver, the following concentrated reaction solutions are prepared:

Activation Concentrate:

11 g of Sn(II) chloride are dissolved in 9 g of concentrated hydrochloric acid and made up to 100 g with demineralised water.

Reduction Concentrate:

5 g of D-glucose and 5 g of D-fructose are dissolved in 100 ml of demineralised water.

Silver Solution:

4 g of potassium hydroxide platelets are dissolved in 10 ml of demineralised water, and 16 ml of concentrated ammonia are added slowly.

4 g of silver nitrate are dissolved in 1 l of demineralised water. The potassium hydroxide solution/ammonia solution is then added dropwise, with stirring, into initially 90% of the silver solution. After the brown precipitate which initially occurs has re-dissolved, the remainder of the silver solution is also added.

2 ml of iodine tincture (5 g of iodine in 95 g of ethanol) are then added to the clear colourless solution.

Activation:

2 g of aluminium oxide platelets having a layer thickness of from 350 to 400 nm are suspended in 50 ml of activation solution and treated at room temperature for 10 minutes. The activation solution comprises 0.1 ml of activation concentrate in 1 l of demineralised water. The material is then filtered off with suction and washed with demineralised water.

Coating:

For the coating, the activated aluminium platelets are suspended in 100 ml of demineralised water, and 10 ml of reduction concentrate are added. This suspension is added to the silver solution with stirring, and the mixture is stirred at room temperature for 30 minutes.

The material is then filtered off, washed with demineralised water and ethanol and dried at 110° C. for 12 hours.

The pigment prepared in this way has a pronounced crystal effect in addition to an attractive silver lustre and hiding power.

Example 2
Application of Metal Layers by Vacuum Vapour Deposition 200 g of aluminium oxide platelets having a layer thickness of from 300 to 350 nm are introduced into the substrate device in a high-vacuum vapour deposition unit with magnetron cathode. After the coating chamber has been pumped out to $10^{-5}$ torr, argon is allowed to flow in to a pressure of $10^{-3}$ torr. The surface of the aluminium target is firstly cleaned for 10 minutes by ion bombardment, with a mask covering the powder.

The coating with aluminium is subsequently carried out at a working pressure of $10^{-3}$ torr for a period of about 150 minutes with constant movement of the powder and with the mask pivoted out, with the duration of the coating being set depending on the desired layer thickness.

The pigment prepared in this way has a pronounced crystal effect in addition to high reflectivity and high hiding power.

What is claimed is:

1. A pigment having metallic luster, comprising a platelet-shaped substrate comprising an aluminium oxide monocrystal and having a thickness of greater than 250 nm and less than 1 $\mu$m which is completely surrounded by a metal layer.

2. A pigment according to claim 1, where the thickness of the substrate is 300–500 nm.

3. A pigment according to claim 1, where the substrate comprises titanium oxide.

4. A pigment according to claim 3, wherein the proportion of titanium oxide is 0.1–4% by weight.

5. A pigment according to claim 1, wherein the substrate comprises particles having a mean particle diameter of 5–60 $\mu$m and a ratio between the mean particle diameter and the mean particle thickness of greater than 20.

6. A pigment according to claim 1, wherein the metal layer comprises aluminium, titanium, chromium, nickel, silver, zinc, molybdenum, tantalum, tungsten, palladium, copper, gold, platinum or an alloy thereof.

7. A pigment according to claim 1, wherein the thickness of the metal layer is from 15–100 nm.

8. A process for preparing a pigment according to claim 1, comprising suspending the substrate in an aqueous and/or solvent-containing medium in the presence of a metal compound and, after addition of a reducing agent, depositing the metal layer on the substrate.

9. A process for preparing a pigment according to claim 1, comprising coating the substrate fluidised in a fluidised bed with a metal obtained by gas-phase decomposition of the corresponding volatile metal compound.

10. A process for preparing a pigment according to claim 1, comprising depositing the corresponding metal on the substrate in a high vacuum by sputtering or thermal vapor deposition, with the substrate being kept in uniform motion during the coating operation.

11. A paint, a surface coating, a printing ink, a plastic, a cosmetic formulation, a ceramic material, a glass, a paper, a dry preparation, a pigment preparation, or a material for a security application comprising a pigment according to claim 1.

12. An automobile comprising a surface coating according to claim 11.

13. A pigment according to claim 1, wherein the substrate has a regular crystal shape and a smooth surface.

14. A pigment according to claim 1, wherein the pigment has an opaque and sparkling metallic appearance.

15. A pigment having metallic luster, consisting essentially of a platelet-shaped substrate comprising aluminum oxide monocrystals and having a thickness of 250 nm–<1 $\mu$m and a surrounding metal layer.

16. A pigment according to claim 1, wherein the metal layer comprises aluminum or silver.

17. A pigment according to claim 1, having a form factor of 50–200.

18. A pigment according to claim 15, wherein the substrate has a thickness of 300–500 nm.

19. A pigment according to claim 1, further comprising a transparent or semitransparent layer allowing at least 10% of the incident light to pass through.

20. A pigment comprising a platelet-shaped aluminum oxide substrate having a thickness of 250 nm–<1 $\mu$m and a surrounding metal layer, wherein the substrate comprises aluminum oxide monocrystals containing titanium oxide.

* * * * *